United States Patent [19]
Masden et al.

[11] Patent Number: 6,099,892
[45] Date of Patent: Aug. 8, 2000

[54] PROTECTIVE COATING FOR DECORATIVE VEGETABLE MATERIAL

[75] Inventors: Phillip R. Masden; Earl J. Naville, Jr., both of Floyds Knobs, Ind.

[73] Assignee: Pumpkin Ltd., Denver, Colo.

[21] Appl. No.: 09/164,977

[22] Filed: Oct. 1, 1998

[51] Int. Cl.⁷ .............................. A01N 3/00; A23L 3/34; A23B 7/16
[52] U.S. Cl. ............................. 427/4; 106/16; 252/382; 252/384; 252/397; 424/407; 426/90; 426/102; 426/133; 426/302; 426/310; 426/532
[58] Field of Search .......................... 427/4; 424/410, 424/407; 252/380, 381, 382, 384, 397; 426/90, 102, 133, 304, 310, 302, 532; 106/16

[56] References Cited

U.S. PATENT DOCUMENTS

| | | | |
|---|---|---|---|
| 2,333,887 | 11/1943 | Redlinger | 427/4 |
| 2,923,095 | 2/1960 | Magimel-Pelonnier et al. | 427/4 |
| 3,098,003 | 7/1963 | Riddell | 427/4 |
| 3,157,964 | 11/1964 | Ferguson et al. | 427/4 |
| 3,669,691 | 6/1972 | De Long et al. | 427/4 |
| 4,748,115 | 5/1988 | Steaffens | 435/21 |
| 5,106,649 | 4/1992 | Spicer et al. | 427/4 |
| 5,330,795 | 7/1994 | Batdorf et al. | 427/393.6 |
| 5,332,427 | 7/1994 | Hayashi et al. | 427/421 |
| 5,338,345 | 8/1994 | Scarborough et al. | 106/2 |
| 5,415,887 | 5/1995 | Chappell | 427/8 |

FOREIGN PATENT DOCUMENTS

| | | | |
|---|---|---|---|
| 553258 | 2/1958 | Canada | 427/4 |
| 1191970 | 5/1970 | United Kingdom | 427/4 |
| 1423121 | 1/1976 | United Kingdom | 427/4 |

OTHER PUBLICATIONS

English Abstract of JA 0034874, Mar. 1977, of Kokai No. 52–34874, Mar. 1977.

*Primary Examiner*—Diana Dudash
*Attorney, Agent, or Firm*—Timothy J. Martin; Michael R. Henson; Mark H. Weygandt

[57] ABSTRACT

The present invention is directed to a composition adapted to be applied to coat a surface area of a vegetable in order to retard environmental degradation thereof. The composition comprises a film-former, a fungicide and a thickener distributed in a carrier liquid. The fungicide may be present in less than one percent (1%) by weight. The composition may include a pH buffer operative to maintain the pH of the mixture between 8.5–10.5. The film-former is operative to coalesce to form a film covering the surface area of the vegetable which is operative to retard dehydration thereof. The fungicide is entrapped throughout the film and is operative to inhibit mildew and fungus growth thereon. The present invention also provides a method of formulating a composition according to the present invention, as well as a method of protecting a decorative vegetable material using a composition according to the present invention.

41 Claims, No Drawings

PROTECTIVE COATING FOR DECORATIVE VEGETABLE MATERIAL

FIELD OF THE INVENTION

This invention generally relates to the protection of decorative vegetable material from environmental degradation. More particularly, though, this invention concerns a composition for coating and protecting the fleshy shell of carved pumpkins, as well as a method therefor. This invention also concerns a process for formulating such a composition.

BACKGROUND OF THE INVENTION

Pumpkin carving has long been one of the several ways in which Halloween is celebrated. Traditionally, pumpkin carving involves the removal of a portion of the pumpkin shell surrounding the stem, removal of the seeds and fibers contained in the pumpkin and carving humorous, grotesque or other decorative features in the pumpkin shell by removing fleshy portions of the shell to obtain the desired appearance. Internal illumination is then provided by a candle. This illumination results in a glowing decorative pattern.

Carved pumpkins are often placed on display indoors or outdoors during the days surrounding Halloween. It is generally desired that such a carved pumpkin will maintain its appearance for a significant time period. One problem with preserving the appearance of a carved pumpkin is that, over time, the fleshy shell of a carved pumpkin will degrade from the effects of environmental factors acting upon it. A carved pumpkin may dry out over time, causing the shell to shrink and the design carved therein to become warped. Mildew, mold and fungus may begin to grow thereupon, causing further degradation and an unsightly appearance, as well as creating difficulties in disposing of the degraded pumpkin shell. Further, outdoor temperature fluctuations can cause periodic freezing and thawing of the pumpkin shell, which can rapidly break down cell material, causing additional degradation and detriment to the appearance of the carved pumpkin. It should be noted that other vegetables (such as squash), as well as fruit, which may also be hollowed out and carved into decorative configurations, can be subject to similar environmental degradation.

An attempt to solve the problem of carved pumpkin degradation is found in the Pumpkin Dunk'N® product, patent pending, produced by Concept Marketing, P.O. Box 1705, Santa Rosa, Calif. 95402. This product utilizes a chemical mixture of calcium hydroxide and sodium tetraborate pentahydrate as a pickling agent and fungicide. The pumpkin to be preserved must—after cleaning out the pumpkin interior but before carving the pumpkin—be initially submerged for a period of 12 to 24 hours in a solution of the chemical mixture and water. After this period, the pumpkin must be washed and then carved into the configuration desired. Within two days subsequent to carving the pumpkin, it must again be immersed in the solution for 4 to 8 hours. The pumpkin must thereafter be immersed in the solution for at least four hours every 3 days, in order to maintain the preservation.

A number of problems with such a product become apparent. First, the active chemical of the product, sodium tetraborate pentahydrate, can be very toxic. Ingestion of 5 to 10 grams of sodium tetraborate pentahydrate "by young children can cause severe vomiting, diarrhea, shock, death." See Budavari et al., *The Merck Index,* Merck & Co., Inc., 11th Ed., p. 1358, 1989, citing R. E. Gosselin et al., *Clinical Toxicology of Commercial Products,* William & Wilkins, Baltimore, 4$^{th}$ Ed., 1976. It is contemplated that the carving of pumpkins, and accordingly the preservation thereof, might be conducted by families and in the presence of small children. It would be undesirable to use such a product in a manner wherein small children might obtain access thereto.

Second, the method proposed for using the product requires repeatedly immersing the pumpkin in 3 gallons of the prepared solution over a substantial period of time. Because the entire contents of the product make only 3 gallons of solution, it is contemplated that users of the product will be required to store the solution in or around their household over a period of time. Given the toxicity described above, such storage could prove difficult when small children might have access to the prepared solution.

Finally, the use of the product requires first carving out the seeds and pulp of the pumpkin interior, then immersing the pumpkin in the prepared solution for a period of 12 to 24 hours prior to finishing the carving of the pumpkin. Many families have a tradition of performing all of the steps of carving a pumpkin together in one evening. The manner of use of the Pumpkin Dunk'N® product would require families to break up those steps over at least two days. This would further create the requirement of preparing and cleaning up a carving site multiple times; an additional hassle given the traditional messiness of pumpkin carving.

Accordingly, it is desirable to provide a relatively safe and efficient method of preventing or retarding environmental degradation of carved vegetable material, such as carved pumpkins. There is thus a need in the industry for a relatively safe, easy to apply composition and method for application of the composition to a carved vegetable material which are operative to prevent or retard environmental degradation thereof. Moreover, there is a need for an efficient method of formulating such a composition. The present invention satisfies these needs and provides these benefits.

OBJECTS AND SUMMARY OF THE INVENTION

It is an object of the present invention to provide a method of protecting the fleshy shell of a carved vegetable, so as to prolong the decorative life thereof.

It is a further object of the present invention to provide a relatively safe composition, and efficient method of formulating such a composition, which can be easily applied to a decorative vegetable material, such as a pumpkin, and which is operative to prevent or retard environmental degradation thereof.

A further object of the present invention is to provide a method of protecting a decorative vegetable material from environmental degradation thereof by applying a coating product operative to extend the useful life of the decorative vegetable material.

It is a further object of the present invention to provide a composition that can be applied to a carved pumpkin as a coating which is operative to extend the useful life of the carved pumpkin by making it less susceptible to shrinkage.

It is another object of the present invention to provide a relatively safe, sprayable coating product for carved pumpkins which extends the attractive appearance thereof by making the pumpkin less susceptible to environmental factors, such as dehydration.

It is still another object of the present invention to provide a coating product for decorative vegetable material meeting applicable safety guidelines and government regulations for the use thereof.

It is a further object of the present invention to provide a cost-effective composition and method of formulating the composition, and a process for protecting a carved pumpkin by applying the composition to the carved pumpkin as a coating therefor, which is operative to extend the decorative life of the carved pumpkin.

Accordingly, a composition is provided which is adapted to be applied to coat a surface area of a vegetable in order to retard environmental degradation thereof. The composition comprises a film former, a fungicide, a thickener and a carrier liquid. The film former, fungicide, and thickener may be distributed in the carrier liquid by dissolution, suspension, dispersion or other means as appropriate. The film former is operative to coalesce, after application to the surface area of the vegetable, to form a film which is adapted to cover the surface area of the vegetable. The film former is further operative to retard dehydration of the vegetable. The fungicide becomes entrapped throughout the film and is operative to inhibit mildew and fungus growth on the film.

The film former may consist of a film-forming dispersion resin polymer in a liquid. The dispersion resin dries by evaporation of the liquid and forms a resultant polymeric film by particle coalescence on the exposed surfaces of the pumpkin. Such polymeric film is operative to coat all or substantially all of the exposed flesh of the pumpkin, or other decorative vegetable material, so as to retard dehydration thereof. It should be understood that the exterior surface portions of the pumpkin, as well as the interior surface portions of the pumpkin that become exposed after carving, may be coated by the film. It is contemplated, however, that only the interior surface portions of exposed flesh need be coated.

The fungicide is entrapped in the polymeric film and inhibits mildew, mold or fungus growth on the surface of the film. The fungicide protects the polymeric film that coats the pumpkin from fungicide growth thereon. The film, in turn, protects the pumpkin by coating all or substantially all of the exposed flesh (the exposed interior surfaces, and optionally the exterior surfaces, as well) of the decorative vegetable material, and inhibiting environmental exposure thereof.

The thickener is a modified cellulosic material which is present in an amount that provides the best balance of sag resistance, which prevents running, and sprayability, for ease of application. A desired consistency may be determined wherein the mixture has sufficient sag resistance such that it will not run off of the pumpkin prior to coalescence of the film former, yet wherein the mixture is sufficiently sprayable through a spray applicator device.

The mixture further includes a carrier liquid which may alternatively comprise water or an organic liquid, such as a mineral oil, or additional components, such as an anti-freeze agent, defoamer, preservative, and/or a pH buffer. The anti-freeze agent, defoamer, preservative, and pH buffer may be distributed in the carrier liquid by dissolution, suspension, dispersion or other means as appropriate.

The anti-freeze agent is operative to provide freeze and thaw resistance to the mixture during shipping, and to slow the drying process. Several alternatives for the anti-freeze agent are available, balancing cost and effectiveness considerations. The defoamer assists in formulation of the mixture in that it prevents soapiness or excessive bubble formation. At least two varieties of defoamer are available. The preservative inhibits bacteria growth in the liquid material during storage and shipment. Several preservative alternatives are available; however, safety considerations must be taken into account. The pH buffer improves the stability of the mixture and assists water retention. Several types of slow amines are available to buffer the mixture.

A method of formulating the mixture is further provided, including steps for efficiently combining the mixture's components. A film-former, anti-freeze agent and defoamer may first be mixed with a carrier liquid therefor to form a first mixture. A preservative may be added to the first mixture during agitation thereof. A second mixture can then be added to the first mixture to form an intermediate composition, wherein the second mixture can include a carrier liquid, a thickener, and a pH buffer. Alternatively, the thickener may be added directly to the first mixture. A fungicide may be added to the intermediate composition during agitation thereof.

The order for adding components is somewhat flexible, in that the goal is to blend all components into a homogenous mixture. However, physical limitations must be taken into consideration, such as excessive bubble formation of the film former and possible problems with polymer coagulation in the presence of carrier solvents used to transport the fungicide. Accordingly, a preferred order is provided for mixing the components to form the composition.

Additionally, a method is provided for protecting a carved pumpkin or other decorative vegetable material comprising steps of carving the pumpkin, applying the composition to coat the remaining fleshy shell of the pumpkin, and allowing the film former to coalesce. The coalescence process allows the composition to form a film coat covering the pumpkin, having the fungicide entrapped therein, which is then operative to retard dehydration and shrinkage of the carved pumpkin, as well as to inhibit mildew, mold and fungus growth on the surface of the film.

These and other objects of the present invention will become more readily appreciated and understood from consideration of the following detailed description of the exemplary embodiments of the present invention, in which:

DETAILED DESCRIPTION OF THE EXEMPLARY EMBODIMENTS

The present disclosure is broadly directed to a chemical composition and method of formulating the same. More specifically, the present invention concerns the protection of decorative vegetable material, such as a carved pumpkin, by application of a chemical composition operative to prevent or retard environmental degradation so as to prolong the useful life thereof.

A. Chemical Composition

An exemplary embodiment of the chemical composition is illustrated by Table 1, as follows:

TABLE 1

| Component | Weight % |
| --- | --- |
| Film Former | 20–45 |
| Fungicide | <1.0 |
| Thickener | <1.0 |
| Carrier Liquid | 53–<80 |

Table 1 shows the composition by weight of an exemplary embodiment of the invention. The film former is present in the solution in a weight percentage of between twenty percent (20%) and forty-five percent (45%). The fungicide and thickener are present in the mixture in small concentrations less than one percent (1%) each. The carrier liquid makes up the remaining balance composition of the solution.

The preferred embodiment of the chemical composition is set forth in Table 2, as follows:

TABLE 2

| Component | Chemical Substance | Pounds | Gallons |
|---|---|---|---|
| Film Former | styrene acrylic resin, 50% colloidal dispersion in water | 54.40 | 5.939 |
| Fungicide | 3-iodo-2-propynyl butyl carbamate, 20% by weight in carrier solvents | 0.80 | 0.093 |
| Thickener | modified cellulose material | 0.04 | 0.004 |
| Carrier Liquid: | | | |
| Anti-freeze agent | propylene glycol | 2.00 | 0.232 |
| Defoamer | silica fluid/silicone oil | 0.30 | 0.041 |
| Preservative | 50% solution of bicyclic oxazolidines in water | 0.20 | 0.022 |
| pH Buffer | 2-amino-2-methyl-1-propanol | 0.20 | 0.025 |
| Water | n/a | 42.06 | 5.049 |
| TOTAL: | | 100.0 | 11.405 |

The preferred film former is a dispersion resin of a styrenated acrylic resin in water. The film former chosen is preferably UCAR 461, which is a tradename for a styrenated acrylic resin provided as a fifty percent (50%) colloidal dispersion in water, and is produced by Ucar Emulsion Systems, a division or subsidiary of Union Carbide Chemicals and Plastics, Co., Inc., located at 2326 Lonnecker Drive, Garland, Tex. 75041, and at 2043 Steel Drive, Tucker, Ga. 30084. It is preferable that the film forming polymer (the styrene acrylic resin, in the case of UCAR 461) be present in the mixture in a weight percentage of between twenty percent (20%) and forty-five percent (45%) of the total composition.

The film former is operative to hold moisture in the decorative vegetable matter after application of the composition, and to inhibit environmental exposure of the decorative vegetable matter. The preferred film former is a dispersion resin that dries by evaporation of water, causing the polymeric beads suspended therein to coalesce to form a polymeric film. However, the ordinarily skilled artisan would understand that other varieties of film formers could be used as well.

Preferably, the film former has a low minimum film forming temperature, so that an additional solvent need not be used to assist particle coalescence as the water evaporates. Generally, the minimum film forming temperature of the chosen film former should be less than expected ambient conditions. In the case of UCAR 461, the minimum film forming temperature is approximately minus seven (−7) degrees Fahrenheit. It should be noted that certain solvents—the addition of which might be necessary if a compound with a higher minimum film forming temperature is used—could undesirably react with other components of the mixture.

The fungicide inhibits mildew, mold or fungus growth on the surface of the film. The chosen fungicide is preferably Polyphase P20T, which is a tradename for a fungicide distributed by Troy Corp., located at 8 Vreeland Rd., P.O. Box 955, Florham Park, N.J. 07932. Polyphase P20T is produced as a twenty percent (20%) by weight composition of 3-iodo-2-propynyl butyl carbamate (the active ingredient) in two carrier solvents, dipropylene glycol monomethyl ether and 2,2,4-trimethylpentane-diol-1,3 monoisobutyrate. Polyphase P20T is registered with the Environmental Protection Agency by Troy Corp. to protect coatings. Here, the active ingredient, 3-iodo-2-propynyl butyl carbamate, protects the coating formed by the film former on the decorative vegetable material. Care should be taken to limit the use of the fungicide to concentrations within the Environmental Protection Agency's legal maximums for interior coatings. In the case of Polyphase P20T, the fungicide should not be added to the mixture in a weight percentage greater than 0.8 percent, the legal maximum for this solution as registered with the Environmental Protection Agency.

The ordinarily skilled artisan would recognize that other fungicides or other forms of distribution of the preferred fungicide could be utilized. For example, 3-iodo-2-propynyl butyl carbamate is further provided by Troy Corp. in other distribution forms, wherein the weight percentage of the active ingredient in the carrier liquid is greater than twenty percent (20%). Care should be taken, however, to comply with Environmental Protection Agency registered maximum concentrations for use with interior coatings for any variety or distribution form of fungicide used. It is contemplated that the active fungicide ingredient would not be present in the composition in a weight percentage greater than one percent (1%).

The thickener may consist of a modified cellulosic material. The chosen thickener is preferably Natrosol Plus 330, a tradename for a modified cellulose material produced by Aqualon Co., located at 2711 Centerville Rd., P.O. Box 15417, Wilmington, De. 19850-5417. The level added should be determined by the best balance of sag resistance versus sprayability. Sag resistance is a measure of a mixture's viscosity or runniness. Sufficient thickener should be added until a desired consistency is reached. If the mixture is to be applied to the decorative vegetable material by spray mechanism, care should be taken that the mixture's consistency is not made so thick as to become inoperable in the spray applicator. However, the mixture should be thick enough that it will adhere to the decorative vegetable material, without running, long enough for the film former to cure by evaporation of the water or liquid in which the polymer is suspended. In the case of Natrosol Plus 330 in the preferred embodiment, approximately 0.04 percent by weight is incorporated into the mixture.

The carrier liquid may be formulated in variations depending upon the parameters desired. The carrier liquid may include an anti-freeze agent, defoamer, preservative, pH buffer and/or water or an organic liquid, such as a mineral oil. The anti-freeze agent and the preservative are primarily for storage purposes. The pH buffer and defoamer assist in the formulation and stability of the composition. The components of the carrier liquid should be selected such that the desired levels of freeze resistance, hindrance of bubble formation, pH stability, and repression of bacteria growth are achieved.

The anti-freeze agent, preferably propylene glycol, provides freeze and thaw resistance during storage and shipping. It also assists in slowing the drying process by holding in moisture. Alternative anti-freeze agents include ethylene glycol and dipropylene glycol, as well as other compounds which the ordinarily skilled artisan would understand to be employable as anti-freeze agents. Ethylene glycol is less costly and more effective than propylene glycol, but less safe. Dipropylene glycol is somewhat more effective than propylene glycol, but more costly and less available. Such materials may be obtained from Ashland Chemical's Chemical & Solvents Division, located at P.O. Box 2219, Columbus, Ohio 43216, and at 600 Oakmont Lane, Chicago, Ill. 60521, among other manufacturers.

Sufficient amounts of anti-freeze agent should be added to the mixture to resist freeze damage to the emulsion during shipment and storage that could occur as a result of ice formation in the mixture. The formation of ice crystals in the mixture during storage can break surfactant bonds in the film former, thereby destroying the functionality thereof. The proper amount of any particular anti-freeze agent to use can be determined by utilizing several test freezes and thaws, in order to measure the mixture's resistance to freeze damage. The level of any particular anti-freeze agent could be increased for assurance of effectiveness; however, at additional expense. Preferably, one percent (1%) to ten percent (10%) by weight of propylene glycol should be added to the composition.

The defoamer is helpful during the formulation of the mixture to prevent the formation of excessive bubbles. The chosen defoamer is preferably Deefo 1020 F, a tradename for a defoamer manufactured by Ultra Additives, Inc., located at 460 Straight St., Paterson, N.J. 07501. The components of the mixture, especially the film former, have a tendency to exhibit soapiness characteristics during agitation, wherein excessive bubble formation may be observed. Such soapiness accompanied by bubble formation can interfere with the addition of further components to the formulation. The addition of a defoamer breaks up bubbles formed by agitation of the mixture, and allows the continued addition of components to the mixture.

Generally, there are two classes of defoamers. The first class encompasses a silicone oil adsorbed onto clay or silica particles that are dispersed in mineral oil. The second class of defoamer encompasses silica fluids. Within each class there are numerous potential alternatives pending efficacy. Preferably, Deefo 1020 F is present in the preferred embodiment in 0.30 percent by weight.

The preservative is operative to inhibit bacteria growth in the liquid material during storage. The chosen preservative is preferably Nuosept 95, a tradename for a preservative manufactured by Huls America, Inc., located at Two Turner Pl., P.O. Box 365, Piscataway, N.J. 08855. Nuoseopt 95 is a fifty percent (50%) solution of bicyclic oxazolidines in water. The ordinarily skilled artisan would understand that potential alternative preservatives exist. Care should be taken that any legal maximum concentrations set by the Environmental Protection Agency are observed. Preferably, Nuosept 95 is present in the preferred embodiment in 0.20 percent by weight.

The pH buffer improves stability and water clean up (helps to keep the solution wet for a longer period of time) of the mixture. The chosen pH buffer is preferably AMP 95, a tradename for an amine manufactured by Angus Chemical Co., located at 1500 E. Lake Cook Rd., Buffalo Grove, Ill. 60089. The pH buffer is operative to buffer the pH of the mixture for stability of the composition. Preferably, the pH of the mixture is maintained at approximately 9.0, near the pH typical of latex paints. While a pH of approximately 8.5 to 10.5 is adequate, the target pH of the mixture is 9.0 to 9.5.

Numerous amines are available as alternatives for the pH buffer. Care should be taken to choose an amine having a slow evaporation rate. AMP 95 incorporates 2-amino-2-methyl-1-propanol; however, other amines having slow evaporation rates, such as DMEA, could also be used. Preferably, AMP 95 is present in the preferred embodiment in 0.20 percent by weight.

It should be noted that many of the above named compounds are trademarks for particular substances available through chemical suppliers, and as such have been more fully described herein. Alternative chemicals may be substituted for the above components, as would be understood by the ordinarily skilled artisan. Further, alternative supplies of the above trademarked substances could be used, where available, provided the manner of distribution, such as the actual weight percentage of the active and inactive ingredients in the mixture, is taken into account when formulating the composition.

B. Formulation Process

With the above composition in mind, a preferred manner of formulating the composition is provided as shown in Table 3, as follows:

TABLE 3

| | Pounds | Gallons |
| --- | --- | --- |
| Add in indicated order: | | |
| Film former (UCAR 461) | 54.40 | 5.939 |
| Water | 10.00 | 1.200 |
| Anti-freeze agent (propylene glycol) | 2.00 | 0.232 |
| Defoamer (Deefo 1020) | 0.30 | 0.041 |
| Add slowly with agitation: | | |
| Preservative (Nuosept 95) | 0.20 | 0.022 |
| Premix next three ingredients: | | |
| Water | 2.00 | 0.240 |
| Sift in slowly with agitation: | | |
| Thickener | 0.04 | 0.004 |
| (Natrosol Plus 330) | | |
| Mix 5 minutes and add: | | |
| pH buffer | 0.20 | 0.025 |
| (AMP 95) | | |
| Mix 15 minutes until thickened and add to batch. | | |
| Add slowly with agitation: | | |
| Fungicide (Polyphase P20T) | 0.80 | 0.093 |
| Mix until uniform and add: | | |
| Water | 30.06 | 3.609 |
| TOTAL: | 100.00 | 11.405 |

In general, the order in which the ingredients are added is somewhat flexible in that the components must be blended into a homogenous mixture. It is possible to add all of the described components, or to selectively incorporate desired components for particular attributes. However, when formulating the mixture, some care should be taken in the method by which the components are added. To avoid potential problems with ingredient and solvent interactivity, and undesirable bubble formation upon agitation, a preferred method of formulating the mixture is presented. This method avoids undesirable coagulation of the emulsion in the presence of solvents, and permits efficient combination of the components of the composition. The method described creates one-hundred (100) pounds of total mixture; however, amounts may be adjusted by weight percentage or volume as appropriate to create more or less of the desired mixture.

The film former, water, anti-freeze, and defoamer are added in the following order and amounts: First, 54.40 pounds (5.939 gallons) of the film former (a colloidal dispersion of styrenated acrylic), preferably UCAR 461, is added to 10.00 pounds (1.200 gallons) of water. Next, 2.00 pounds (0.232 gallons) of anti-freeze agent, preferably propylene glycol, and 0.30 pounds (0.041 gallons) of defoamer, preferably Deefo 1020 F is added. The resulting solution forms a first mixture comprising the film former, water, anti-freeze agent and defoamer. The first mixture is then agitated for a first interval of time, during which the preservative may be added to the first mixture.

The thickener and the pH buffer can be added as a second mixture, and then the resulting intermediate composition is agitated. Alternatively, the thickener can be added to the first mixture directly by dusting or sieving the thickener into the mixture. In creating the second mixture, several sub-steps are involved. First, 0.04 pounds (0.004 gallons) of thickener, preferably Natrosol Plus 330, are sifted slowly with agitation into 2.00 pounds (0.240 gallons) of water to form a first intermediate mixture. The first intermediate mixture is then mixed for a selected interval of time, preferably five (5) minutes. Next, 0.20 pounds (0.025 gallons) of the pH buffer, preferably AMP 95, is added to the first intermediate mixture to form the second mixture, which is then mixed for another interval of time, preferably fifteen (15) minutes, until the second mixture is thickened. The second mixture is then added to the first mixture to form the intermediate composition.

The thickener itself may be incorporated by three alternative methods. First, the thickener may be added as a two percent (2%) pre-gelled solution, wherein the water is adjusted accordingly. A second alternative method is to slurry the thickener in approximately one half (0.5) gallon of water which has been buffered to a pH of 6.0 to 6.5 with acetic acid, before adding to the mixture. Finally, the thickener may be added directly to the first mixture by dusting or sieving the thickener into the mixture; however, this final alternative tends to result in undesired clumping of thickener particles in the solution.

The intermediate composition is then agitated for a selected interval of time, during which 0.80 pounds (0.093 gallons) of the fungicide, preferably Polyphase P20T, is added and then mixed until uniform. Finally, 30.06 pounds (3.609 gallons) of water is blended in to form a final composition that is homogenous.

It should be noted that variations may be made on the number of components added, the selection of the components themselves, and the manner and order in which the combination occurs. Care should be taken to adjust for any variations in the compositions of the supply chemicals, such as differences in the concentrations of active ingredients in their own carrier substances.

C. Protection Procedure

The invention further is directed to a method of protecting a decorative vegetable material, such as a carved pumpkin. Having obtained the above described composition, one may apply the composition to a carved pumpkin or other vegetable matter having a fleshy shell so as to protect and prolong the life of the vegetable material.

First, a fruit or vegetable is hollowed out by removing seeds and fibrous material through an opening in the fleshy shell. The shell may then be further carved in desired configurations to yield an object comprising the decorative vegetable material, such as a carved pumpkin of the "Jack-O-Lantern" type commonly displayed around the Halloween season. The decorative vegetable material is then contacted with the mixture comprising a film former, a fungicide, a thickener and a carrier liquid. The mixture may be applied directly to the decorative vegetable material by pouring or wiping with an applicator device, or it may be applied by spraying the mixture from a spray applicator mechanism and container, or by other means such as brushing, dipping, etc.

All parts of the vegetable matter to be protected may be coated, such as both the inner and outer portions of the fleshy shell, as well as portions exposed to the environment by design carvings in the sidewall of the fleshy shell. The film former then coalesces during a selected interval of time, by evaporation of the water or organic liquid and any carrier solvents associated with the film former and fungicide, creating a polymeric film on the surface of the decorative vegetable material as a result of the film former's polymeric particle coalescence.

The fungicide, thickener, and non-volatile components of the carrier liquid—the preservative and the clay particles of the defoamer—remain entrapped throughout the polymeric film. The additional components of the mixture—the anti-freeze agent, the pH buffer, and the mineral oil component of the defoamer—having slow evaporation rates, are initially entrapped throughout the polymeric film. These components, however, will evaporate post film-forming, over a subsequent period of time.

The polymeric film covering the exposed portions of the fleshy shell of the pumpkin or other vegetable is operative to retard dehydration of the decorative vegetable material and to inhibit environmental exposure thereof. The fungicide is operative to inhibit mildew, mold and fungus growth on the surface of the polymeric film, thereby further prolonging the useful life of the carved pumpkin. Application of the composition to the decorative vegetable matter may be repeated as necessary to further prolong the life of the material.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A composition adapted to be applied to coat a surface area of a vegetable in order to retard environmental degradation thereof, comprising a film former, a fungicide and less than one percent (1%) by weight of a thickener distributed in a carrier liquid and wherein said film-former is operative, after application to the surface area of the vegetable, to coalesce such that said film former forms a film covering the surface area of the vegetable, wherein said film is operative to retard dehydration thereof and wherein said fungicide is entrapped throughout said film and is operative to inhibit mildew and fungus growth thereon.

2. A composition according to claim 1, wherein the film former comprises a dispersion resin of a liquid and a polymer.

3. A composition according to claim 2, wherein the polymer is a styrene acrylic resin.

4. A composition according to claim 2, wherein the polymer is present in the mixture in a weight percentage of 20 to 28 percent.

5. A composition according to claim 1, wherein the fungicide is 3-iodo-2-propynyl butyl carbamate.

6. A composition according to claim 1, wherein the fungicide is present in the mixture in a weight percentage of no greater than 1 percent.

7. A composition according to claim 1, wherein the thickener is a modified cellulosic material.

8. A composition according to claim 1, including an anti-freeze agent distributed in said carrier liquid.

9. A composition according to claim 8, wherein the anti-freeze agent is selected from a group consisting of ethylene glycol, propylene glycol, and dipropylene glycol.

10. A composition according to claim 8, wherein the anti-freeze agent is present in a weight percentage of 1 to 10 percent.

11. A composition according to claim 8, wherein the anti-freeze agent is operative to retard dehydration of the mixture and to resist freeze damage thereto.

12. A composition according to claim 1, including a pH buffer distributed in the carrier liquid, said pH buffer operative to maintain the mixture at a pH of 8.5–10.5.

13. A composition according to claim 12, wherein the pH buffer is an amine.

14. A composition according to claim 13, wherein the amine is 2-amino-2-methyl-1-propanol.

15. A composition according to claim 1, including a preservative distributed in the carrier liquid, said preservative being operative to inhibit bacteria growth in the mixture.

16. A composition according to claim 15, wherein the preservative comprises bicyclic oxazolidines.

17. A composition according to claim 1, including a defoamer distributed in the carrier liquid.

18. A composition according to claim 17, wherein the defoamer is a silica fluid.

19. A composition according to claim 17, wherein the defoamer is a silicone oil adsorbed onto particles selected from the group consisting of clay and silica, and wherein the particles are dispersed in mineral oil.

20. A method of formulating a composition adapted for application to a decorative vegetable material as a protective coating thereof, comprising the steps of:
  (a) preparing a first mixture which includes a film former distributed in a first carrier liquid;
  (b) preparing a second mixture which includes less than one percent (1%) by total weight of the composition of a thickener in a second carrier liquid, wherein said second carrier is miscible with said first carrier liquid;
  (c) combining said first and second mixture to form an intermediate composition;
  (d) agitating the intermediate composition for a first interval of time; and
  (e) adding less than one percent (1%) by total weight of the composition of a fungicide to the intermediate composition during the first interval of time.

21. A method according to claim 20, wherein the first mixture includes an anti-freeze agent and a defoamer.

22. A method according to claim 20, including the step of agitating the first mixture while adding a preservative thereto prior to combining the first mixture with the second mixture.

23. A method according to claim 20, wherein the second mixture includes a pH buffer.

24. A method according to claim 23, wherein the second mixture is prepared by blending the thickener and the second carrier liquid to form an intermediate mixture and thereafter blending the pH buffer with the intermediate mixture to form the second mixture.

25. A method according to claim 20, wherein the thickener comprises a two percent pre-gelled solution of modified cellulosic material and water.

26. A method according to claim 20, wherein the thickener comprises a modified cellulosic material slurried in water buffered to a pH of 6.0 to 6.5 with acetic acid.

27. A method according to claim 20, including the step of blending the intermediate composition with water after the first interval of time to form a final composition wherein the final composition is homogeneous.

28. A method of protecting a decorative vegetable material, comprising the steps of:
  (a) removing the interior contents of a vegetable so as to yield a hollowed out object comprising the decorative vegetable material;
  (b) contacting the decorative vegetable material with a mixture comprising less than one percent (1%) by weight of a fungicide, less than one percent (1%) by weight of a thickener, and a colloidal dispersion of a film-forming polymer in a liquid, such that the mixture forms a layer covering substantially all of the exposed flesh of the decorative vegetable material to be protected; and
  (c) coalescing the film-forming polymer over a first interval of time so as to form a polymeric film covering substantially all of the exposed flesh of the decorative vegetable material to be protected, wherein the polymeric film is operative to retard dehydration of the decorative vegetable material and to inhibit environmental exposure thereof, and wherein the fungicide becomes entrapped in the polymeric film and is operative to inhibit mildew and fungus growth on the surface thereof.

29. A method according to claim 28 wherein the step of coalescing the film-forming polymer comprises allowing the liquid to evaporate from the mixture.

30. A method according to claim 28, wherein steps (b) and (c) are repeated.

31. A method according to claim 28, wherein the mixture includes a carrier liquid having at least one of a group consisting of an anti-freeze agent, a defoamer having a mineral oil component, a pH buffer, and a preservative.

32. A method according to claim 28, wherein the anti-freeze agent, the pH buffer, and the mineral oil component of the defoamer evaporate after formation of the polymeric film over a second interval of time.

33. A method according to claim 28, wherein the step of contacting the decorative vegetable material with the mixture is accomplished by spraying the mixture onto the decorative vegetable material.

34. A composition according to claim 4, wherein the fungicide is present in the mixture in a weight percentage of no greater than one percent (1%).

35. A composition according to claim 1, wherein the thickener is present in the mixture in a weight percentage of approximately 0.04 percent.

36. A composition according to claim 12, wherein the pH of the mixture is maintained at approximately 9.0.

37. A method according to claim 20, wherein the film former comprises a dispersion resin of a liquid and a polymer, and wherein the polymer is present in the mixture in a weight percentage of 20 to 28 percent.

38. A method according to claim 28, wherein the film-forming polymer is present in the mixture in a weight percentage of 20 to 28 percent.

39. A composition adapted to be applied to coat a surface area of a vegetable in order to retard environmental degradation thereof, comprising a film former, a fungicide and a thickener distributed in a carrier liquid, and including a pH buffer distributed in the carrier liquid and operative to maintain the pH of the mixture at a pH of 8.5–10.5, and wherein said film-former is operative, after application to the surface area of the vegetable, to coalesce such that said film former forms a film covering the surface area of the vegetable, wherein said film is operative to retard dehydration thereof and wherein said fungicide is entrapped throughout said film and is operative to inhibit mildew and fungus growth thereon.

40. A composition according to claim 39, wherein the pH of the mixture is maintained at approximately 9.0.

41. A composition according to claim 39, wherein the pH of the mixture is maintained between 9.6 and 10.5.

* * * * *